(12) United States Patent
Weingard

(10) Patent No.: US 9,794,453 B2
(45) Date of Patent: Oct. 17, 2017

(54) ILLUMINATION APPARATUS INTERPOSABLE DURING EXAMINATION PROCEDURE

(71) Applicant: James A Weingard, Tempe, AZ (US)

(72) Inventor: James A Weingard, Tempe, AZ (US)

( * ) Notice: Subject to any disclaimer, the term of this patent is extended or adjusted under 35 U.S.C. 154(b) by 0 days.

(21) Appl. No.: 14/756,505

(22) Filed: Sep. 11, 2015

(65) Prior Publication Data

US 2016/0100095 A1  Apr. 7, 2016

Related U.S. Application Data

(60) Provisional application No. 62/071,032, filed on Sep. 11, 2014.

(51) Int. Cl.
*H04N 5/225* (2006.01)
*H04N 9/28* (2006.01)
*A61B 19/00* (2006.01)

(52) U.S. Cl.
CPC .......... *H04N 5/2251* (2013.01); *A61B 19/26* (2013.01); *A61B 19/5202* (2013.01); *H04N 5/2256* (2013.01); *H04N 9/28* (2013.01); *A61B 2019/5231* (2013.01)

(58) Field of Classification Search
None
See application file for complete search history.

(56) References Cited

U.S. PATENT DOCUMENTS

| 7,970,269 | B2* | 6/2011 | Nubling | G03B 15/03 396/61 |
| 2001/0038439 | A1* | 11/2001 | Doherty | A61B 3/0008 351/221 |
| 2002/0159621 | A1* | 10/2002 | Callies | A61B 3/13 382/128 |
| 2003/0164953 | A1* | 9/2003 | Bauch | A61B 90/30 356/611 |
| 2006/0119701 | A1* | 6/2006 | King | H04N 7/181 348/14.08 |
| 2007/0203413 | A1* | 8/2007 | Frangioni | A61B 5/415 600/478 |
| 2007/0258248 | A1* | 11/2007 | Duhe | G02B 25/02 362/362 |
| 2011/0264078 | A1* | 10/2011 | Lipow | A61B 90/50 606/1 |
| 2012/0310141 | A1* | 12/2012 | Kornfield | A61F 9/008 604/20 |
| 2013/0163274 | A1* | 6/2013 | Gerber | F21V 7/00 362/558 |

* cited by examiner

*Primary Examiner* — Timothy J Henn
(74) *Attorney, Agent, or Firm* — Tod R. Nissle, P.C.

(57) ABSTRACT

An illumination apparatus comprises a mobile stand, an articulating arm extending outwardly from the mobile stand, an illumination unit mounted on the articulating arm, and a camera mounted on the articulating arm. The camera is mounted on the interior of the illumination unit. The illumination unit is constructed to provide a clear field of view through the illumination unit.

1 Claim, 3 Drawing Sheets

ILLUMINATION APPARATUS INTERPOSABLE DURING EXAMINATION PROCEDURE

This application claims priority based on U.S. Provisional Patent Application Ser. No. 62/071,032 filed Sep. 11, 2014.

This application relates to illumination apparatus.

More particularly, the invention disclosed herein relates to examination apparatus.

In a further respect, the invention relates to illumination apparatus which can be positioned intermediate a surgeon or other individual and a patient or other subject during examination of the subject.

Those of skill in the art have for many years endeavored to discover and produce improved illumination apparatus for use during surgery and other medical and non-medical procedures. Accordingly, it would be advantageous to invent such apparatus.

Therefore, it is a principal object of the instant invention to provide improved illumination apparatus.

Another object of the invention is to provide improved illumination to facilitate the successful examination by an individual of a subject.

These, and further and more specific objects and advantages of the invention will be apparent to those skilled in the art from the following detailed description thereof, taken in conjunction with the drawings, in which.

Briefly, provided in accordance with the invention is an improved method for an individual to examine a subject. The method comprises the step of providing illumination apparatus. The illumination apparatus comprises a portable stand having a body having a top, a bottom, and a width. The stand also includes a plurality of ground engaging wheels mounted on the bottom of the body. The illumination apparatus also comprises a support mounted on said body, extending upwardly from said top of said stand and having a width equal to less than 25% of said width of said body of said portable stand. The illumination apparatus also comprises an articulating arm having a proximate end connected to the support, and having a distal end. The illumination apparatus also comprises an illumination unit mounted on the distal end of the articulating arm. The illumination unit includes a light source extending circumferentially around an open area; a camera mounted in registration with said open area, said camera having a manually adjustable focus and a weight less than 350 grams, and a clear field of view extending completely through said open area and intermediate said circumferential light source. The illumination apparatus is shaped and dimensioned such that the articulating arm can position the illumination unit intermediate the individual and the subject such that the individual can see at least a portion of the subject through said clear field of view. The illumination apparatus also includes a display screen remote from the camera, and a system operatively associated with the display screen and the camera to transmit wirelessly from the camera to the display screen visual representations of the subject produced by the camera. The method also includes the step of adjusting said articulating arm to position said illumination unit intermediate the individual and the subject such that the individual can, if desired, see the subject through said clear field of view; such that the camera is positioned above the subject and is producing visual representations of the subject; and, such that the visual representations produced in (b) (ii) are depicted on the display screen. The ground engaging wheels, the body, the support, and the articulating arm are shaped and dimensioned and form to damp vibrations transmitted into the illumination apparatus from the ground such that the visual representations depicted on the display screen are still.

Figure 1:
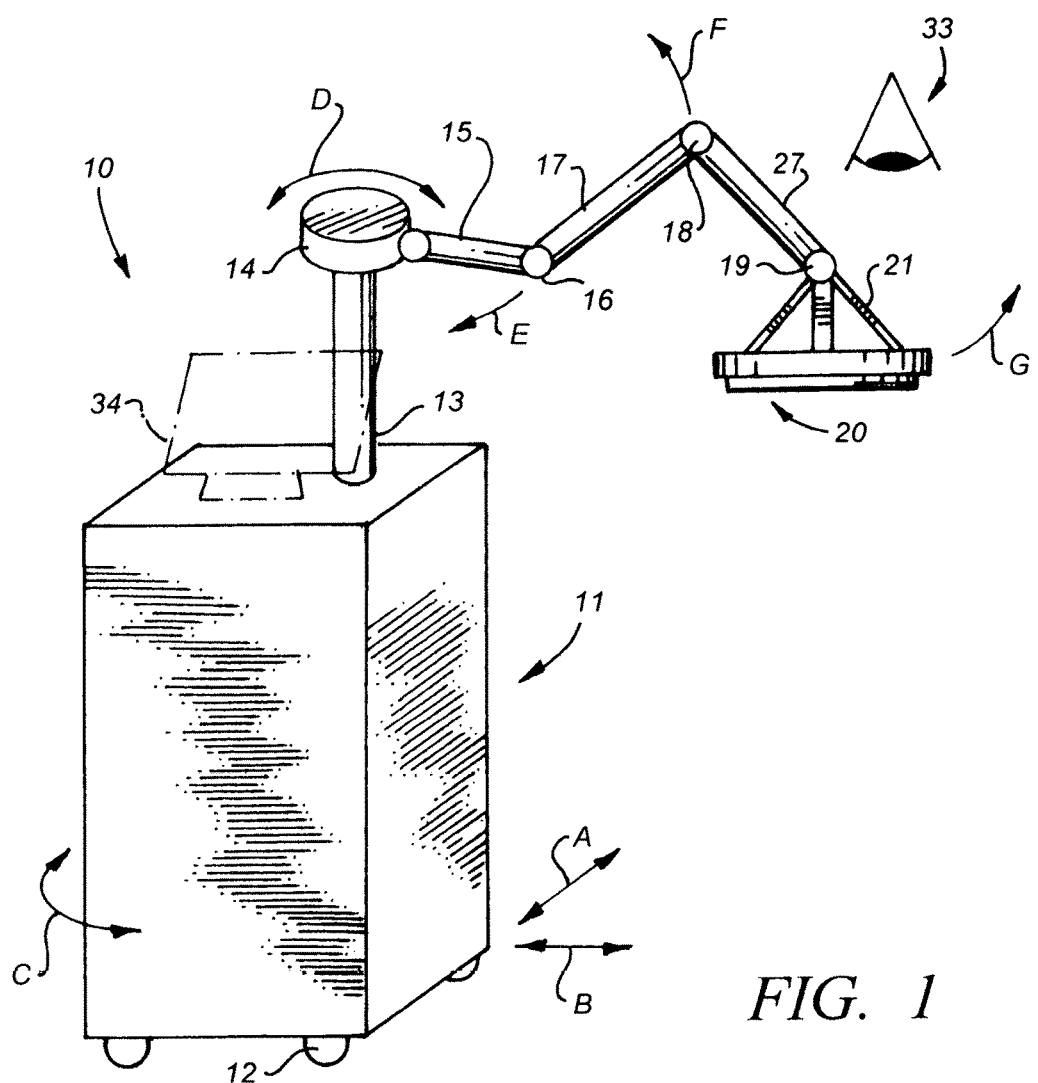
FIG. 1 is a perspective view illustrating apparatus constructed in accordance with the principles of the invention.

Turning now to the drawings, in which like characters refer to corresponding elements throughout the several views, and in which embodiments of the invention are provided by way of illustration and not limitation of the invention, FIG. 1 illustrates illumination apparatus constructed in accordance with the invention and generally indicated by reference character 10. Apparatus 10 includes portable stand 11, although in alternate embodiments of the invention the articulating arm and illumination unit 20 described below are, by constructing and using appropriate structural support apparatus, wall or ceiling mounted. Rollers or casters 12 permit stand to be moved, laterally as indicated by arrows B, forwardly and rearwardly as indicated by arrows A, and rotatably as indicated by arrows C. Stand 11 preferably includes a foot brake (not shown) or some other means of maintaining stand 11 in a desired fixed position on the floor after stand 11 has been rolled to a desired location. In one embodiment of the invention, the "foot brake" comprises a foot operated lock/unlock mechanism which is operatively associated with at least one of the rollers 12, and which when "locked" fixes the roller in place so that it can not move.

Swivel head 14 is rotatably mounted on the distal end of upright support post 13, and can be rotated in the directions indicated by arrows D.

The proximate end of post 13 is connected to the body 11A of stand 11. In FIG. 1, body 11A has an orthogonal shape; however, the shape and dimension of body 11A can vary as desired. In one embodiment of the invention, the proximate end of post 13 is adjustably secured against a selected side 11B, 11C, 11D of body 11A by U-shaped brackets (not shown) which are screwed into said selected side and compress the proximate end intermediate the brackets and the selected side. Loosening the brackets permits the position of post 13 to be adjusted slidably upwardly and downwardly, after which the brackets are again tightened to secure post 13 is a desired position. Any other desired construct can be utilized to permit post 13 (and the distal end of the articulating arm discussed just below) to be upwardly and downwardly adjusted.

An articulating arm includes a proximate end connected to and extends outwardly from head 14 and includes a plurality of elongate structural members 15, 17, 27 attached to and/or interconnected by a plurality of universal joints 16, 18, 19 which permit members 15, 17, 27 and unit 20 to pivot or move in any desired direction E, F, G. The distal end of the articulating arm is connected to illumination unit 20. The articulating arm is adjustable to permit the position of unit 20 to be adjusted upwardly and downwardly through a range at least five feet in height, preferably through a range at least four feet in height, and most preferably through a range at least three feet in height. For example, if the range is three feet and the lowest position to which unit 20 can be adjusted is three feet above the ground, then the highest position to which unit 20 can be adjust is six feet above the ground. The amount by which the articulating arm is extending will, of course, affect how far unit 20 can, practically speaking, be upwardly and downwardly adjusted.

Importantly, once the articulating arm is used to position illumination unit 20, the arm and therefore unit 20 must not travel, but must maintain their fixed position. Small movements, or traveling, of the articulating arm and unit 20 are critical to avoid, if for no other reason that the focus of camera 34 described below can be lost. Consequently, the articulating arm should, in the preferred embodiments of the invention, include means to "tighten" the arm so that while the arm permits movement of the structural members of the arm with respect to one another and therefore permits repositioning of unit 20, once unit 20 is in a desired position, unit 20 and the components of the articulating arm maintain their position. Depending on the construction of the articulating arm, any desired tightening means can be used to adjust the arm to "stiffen" movement of the arm. Such a tightening means ordinarily increases friction between at least certain components in the arm to make the arm better able to maintain a selected position or orientation. As will be noted, the weight of the illumination unit and camera utilized in the invention is also critical.

Figure 2:
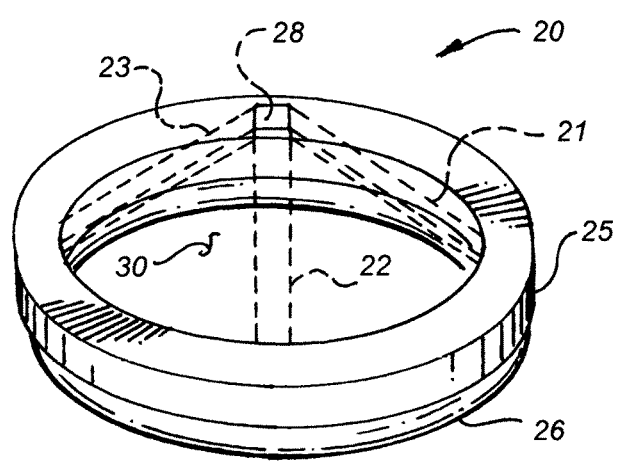
FIG. 2 is a perspective view illustrating an illumination unit comprising part of the apparatus of FIG. 1.

The illumination unit 20 includes a circumferential light source 26 which can, in the manner illustrated in FIG. 2, consist of a circular fluorescent lamp. Light source 26 can also consist of a plurality of LEDs (or any other light producing object or objects) extending around a circumferential path comparable to the path along which the circular fluorescent lamp of FIG. 2 extends. As will be appreciated by those of skill in the art, the circumferential path can be continuous or can consist of spaced apart segments. For example, LED lights could form a U-shaped pattern about a field of view or open area 30; or, the LED lights can be arranged along a pair of spaced apart parallel paths on either side of area 30; and so on.

Light source 26 is mounted on circular frame 25. Legs 21, 22, 23, 24 are each attached at one end to circular frame 25 and at the other end to square panel member 28. Panel member 28 is fixedly attached to universal joint 19 (FIG. 1).

Figure 3:
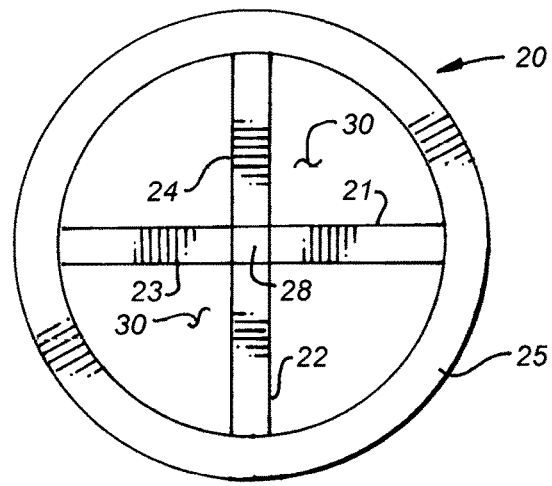
FIG. 3 is a top view further illustrating the illumination unit of FIG. 2; and, FIG. 4 is a side view further illustrating the illumination unit of FIG. 2.

Importantly, when a subject is being viewed, illumination unit 20 affords the viewing individual 3 (FIG. 1) a clear field of view through unit 20 so that the individual can view selected areas of the subject. This is permitted by the field of view 30 which is circumscribed by light source 26 and by frame 25. As can be seen in FIG. 3, only legs 21 to 24 and panel member 28 on unit 20 per se block portions of field of view 30. Large areas of the field of view 30 are, as can be seen in the top view illustrated in FIG. 3, unblocked and allow an individual to completely see through unit 20 in areas which are circumscribed by frame 25 and light source 26. The ability of an individual to see—via field of view 30—portions of a subject permits illumination unit 20 to be positioned intermediate the individual and the subject (by manipulating the articulating arm) which, in turn, permits light source 26 to positioned closer to the subject to better illuminate areas of the subject.

While the invention can be utilized to view a wide variety of subjects including, without limitation, botanical specimens, birds or other animals, insects, fabrics, semiconductors, and mechanical parts, one preferred application of the invention is in the medical field where the invention can be used to examine patients, living or dead. Such examination can occur during routine medical examinations which do not require surgery or can be used during surgery.

Figure 4:
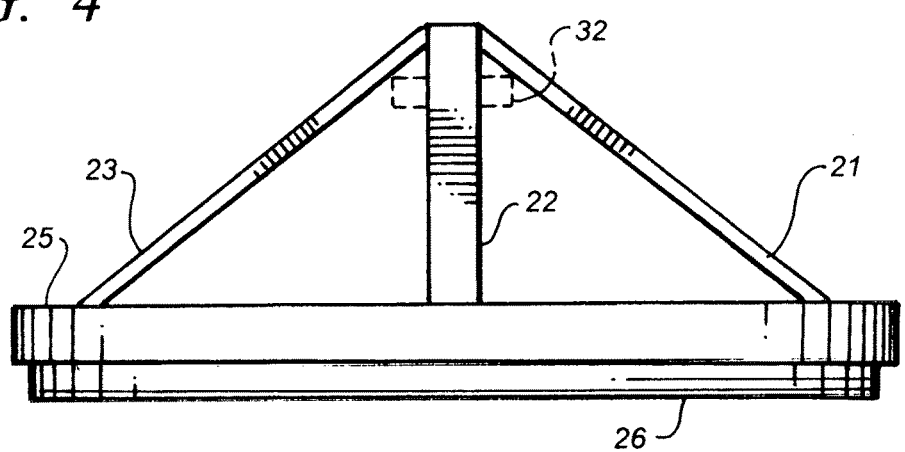

In an alternate embodiment of the invention, a camera 32 is, as shown in FIG. 4, mounted on the illumination unit 20. Still or live action photographs or video taken by camera 32 can be transmitted wirelessly, via wi-fi, or by hard wire to a display monitor 34 or computer for viewing real time on the display screen of the computer. Photographs or video from camera 32 can be stored on a computer or other video recording device.

In one preferred embodiment of the invention, camera 32 includes a lens which can be manually operated to focus the camera on a selected area of the subject. This is a particularly advantageous and important feature of the invention because as an examination progresses, the distance of the selected area of the subject from camera 32 or from the eyes of the examining individual. For example, during surgery on a patient when an incision is initially made the point at which the incision is made may be a selected distance from the top of the operating table. After the incision is made, however, the portion of the patient's body upon which surgery is being performed real time may be closer to the top of the operating table (and further from camera 32), which necessitates refocusing of the lens of camera 32. Similarly, if the position of illumination unit 20 is changed or adjusted, the distance of unit 20 from the patient can change, requiring that the lens of camera 32 be refocusing. Another reason why the ability to refocus manually the lens of camera 32 is important for a surgeon is that the surgeon may move from a first particular area of the patient's body to a second area which is a relatively short distance from the area of the body initially worked on by the surgeon, and the second area is near the first area and lies in the field of view of the camera of the first area, but is a different distance from camera, which requires that the camera lens be refocused so the surgeon can clearly see the second area.

Camera 32 can also, if desired, include an auto focus feature or a feature to adjust the iris of the camera.

Manual focusing of camera 32 can includes means to manually adjust the aperture to increase or decrease the depth of the field of vision.

Power to operate camera 32, light source 26, and/or computer 34 can be supplied by battery or any other desired power source. The battery can be rechargeable.

Mounting the articulating arm and illumination unit on top of a mobile stand is important in the practice of the invention because it facilitates moving and adjusting the position of the articulating arm and illumination unit, it provides storage space for a computer 34 and other equipment utilized by a surgeon, and the height of the mobile stand functions to initially position the illumination unit and articulating arm at a desired height. Further, and importantly, the size of the mobile stand is significant because the stand serves as a "sink" to absorb vibration emanating from the floor and because the stand serves as ballast to counter torque forces generated by the articulating arm and illumination unit 20. Consequently, the height of the mobile stand is in the range of two and one half to five feet, preferably three feet to four and one half feet. The weight of stand 11 is at least one hundred pounds, preferably at least one hundred and twenty five pounds, more preferably at least one hundred and fifty pounds, and most preferably at least two hundred pounds.

The articulating arm is sized to permit the distal end of the arm (the end attached to illumination unit 20) to extend a horizontal distance of at least three feet from support 13, preferably at least four feet from support 13, and more preferably at least five feet. The maximum distance that the distal end of the articulating arm would extent from support 13, is presently in the range of seven to eight feet.

When portions of the articulating arm and when illumination unit 20 extend outwardly from stand 11, they generate a torque force which acts on stand 11. One principal important functions of stand 11 is, as noted, for it to have sufficient size and weight to prevent the torque force from tipping over stand 11. The width and depth of stand 11 are at least one and one-half feet, preferably at least two feet, more preferably at least two and one half feet, and most preferably at least three feet. The currently produced model utilizes a stand which has a depth and width of two feet.

One important function of the invention which was inadvertently discovered during the construction of the invention is the ability of the invention to dampen vibrations. One reason for this particular function is believed to be mounting the body 11A on wheels. The wheels have limited point contact with the ground in contrast to the much greater contact the body 11A would have if it was not provided with wheels. Another reason for the damping function is believed to be the size and weight of body 11A and of the weight of ballast, of a battery, or of other components stored in or on body 11A. The mass provided by such weight is believed to help absorb vibration. A further reason for the damping function of the invention is believed to be the size differential between body 11A and post 13. Post 13 is much smaller than body 11A, has limited contact with body 11A, and therefore appear less likely to receive a significant magnitude of vibrational energy from body 11. Still another reason for the damping function of the invention is believed to be the size of the structural components in the articulating arm. These components are much smaller than body 11A and appear unlikely to receive from post 13 vibrational energy of a significant magnitude. Still a further reason for the damping function of the invention is believed to be number of components in the articulation arm. Each components is believe to act in its own right to absorb vibrational energy.

One significant virtue of the invention is the ability for auxiliary persons other than the individual who is primarily examining a subject to view on display 34 images produced by camera 32 so such auxiliary individuals can follow and participate in the examination. The images on display 34 may also be viewed by the primary examination individual in real time or later recalled for review. The images may also be viewed remotely using a video conferencing system or software.

Storing in a computer, server, etc. images produced and transmitted by camera 32 provides an opportunity to produce a record of the examination and to review later, if wished, the record.

Having described my invention in such terms as to enable those skill in the art to understand and practice it, and having described the presently preferred embodiments thereof, I claim:

1. A method for an individual to examine and perform surgery on a subject, comprising the steps of
   (a) constructing a vibration dampening illumination apparatus comprising
      (i) a vibration dampening portable stand having
         a body having a top, a bottom, a depth of at least two feet, a width of at least two feet, and a weight of at least one hundred pounds, and
         a plurality of ground engaging wheels mounted on said bottom, and
      (ii) a support extending upwardly from said top of said stand and having a width less than said width of said body of said portable stand,
      (iii) an articulating arm having
         a proximate end connected to said support, and
         a distal end,
      (iv) an illumination unit including a light source extending circumferentially around an open area,
      (v) a plurality of spaced apart support arms outwardly extending from said distal end and interconnecting said distal end and said illumination unit,
      (vi) a camera centrally mounted intermediate said support arms and above said open area and said circumferential light source, said camera having a manually adjustable focus,
      (vii) a clear open field of view extending from above said illumination unit, past said support arms and said camera, completely through said open area, and intermediate and past said circumferential light source,
      said articulating arm being shaped and dimensioned such that said articulating arm can position said illumination unit intermediate the individual and the subject such that the individual can see at last a portion of the subject through said clear field of view,
      (viii) a display screen remote from said camera,
      (ix) a system operatively associated with said display screen and said camera to transmit from said camera to said display screen visual representations of the subject produced by said camera;
   (b) positioning said portable stand and adjusting said articulating arm to position said illumination unit intermediate the individual and the subject in a first operative position such that
      (i) the individual can see an incision area on the subject through said clear field of view,
      (ii) said camera is positioned above the subject and is producing visual representations of the subject, and
      (iii) the visual representations produced in (b)(ii) are depicted on said display screen;
   (c) making an incision in said incision area;
   (d) adjusting said articulating arm to position said illumination unit intermediate the individual and the subject in a second operative position closer to the subject than when said illumination unit is in said first operative position; and
   (e) manually adjusting the focus of said camera,
   said ground engaging wheels, said body, said support, and said articulating arm being shaped and dimensioned and formed to dampen vibrations transmitted into said illumination apparatus from the ground when said incision is made.

* * * * *